US006554777B1

(12) United States Patent
Hein, Jr.

(10) Patent No.: US 6,554,777 B1
(45) Date of Patent: Apr. 29, 2003

(54) MULTI-SITE SKIN-TEST SYSTEM AND METHOD (76) Inventor: Gary L. Hein, Jr., Windy Hill Farm R.R. 1, Box 75, Oakley, IL (US) 62552

( * ) Notice: Subject to any disclaimer, the term of this patent is extended or adjusted under 35 U.S.C. 154(b) by 0 days.

(21) Appl. No.: 09/945,271

(22) Filed: Aug. 31, 2001

(51) Int. Cl.[7] .................................................. A61B 5/00
(52) U.S. Cl. ....................................................... 600/556
(58) Field of Search ............................ 600/556; 604/47, 604/46; 206/366, 142, 143, 153, 161, 168, 169, 558, 438, 538, 559; 294/87.2; 220/23.4, 523, 526

(56) References Cited

U.S. PATENT DOCUMENTS

| 2,522,309 | A | * | 9/1950 | Simon ........................ 600/556 |
| 3,289,670 | A | * | 12/1966 | Krug et al. .................. 600/556 |
| 3,556,080 | A | * | 1/1971 | Hein ........................... 600/556 |
| 4,448,452 | A | * | 5/1984 | Wood ......................... 294/87.2 |
| 4,453,825 | A | * | 6/1984 | Galy ............................ 604/47 |
| 5,396,989 | A | * | 3/1995 | Hein ........................... 206/366 |
| 5,647,371 | A | * | 7/1997 | White et al. ................. 600/556 |
| 5,692,518 | A | * | 12/1997 | Baker et al. ................. 600/556 |
| 5,738,108 | A | | 4/1998 | Hein |
| 5,792,071 | A | | 8/1998 | Hein |
| 6,095,988 | A | * | 8/2000 | Doll et al. .................. 600/556 |
| 6,206,838 | B1 | * | 3/2001 | Doll et al. .................. 600/556 |
| 6,221,027 | B1 | * | 4/2001 | Pitesky ....................... 600/556 |
| 6,258,041 | B1 | * | 7/2001 | Pitesky ....................... 600/556 |

OTHER PUBLICATIONS

Instructions For Using the Multi–Test® Dipwell® Tray Lid Label.
Instructions For Using the Multi–Test® II Dipwell™ Tray.

* cited by examiner

Primary Examiner—Eric F. Winakur
Assistant Examiner—N. Veniaminov
(74) Attorney, Agent, or Firm—Banner & Witcoff, Ltd.

(57) ABSTRACT

A multi-site skin-test system including a reservoir tray and strips of interconnected reservoir caps inserted into upper portions of the reservoirs. The caps each include a generally conically shaped hole. Connection members connect the caps of a strip to one another. The strips of caps are pressed into tightly fitting upper portions of reservoirs having upwardly facing ledge surfaces for supporting downwardly facing bottom surfaces of the caps. The outer side surfaces of the caps and the inner surfaces of the upper portions of the reservoirs are substantially the same size to provide a tight fit. A tray lid includes a downwardly extending ridge that cooperates with the tray to prevent the lid from being placed onto the tray backwards. The ridge also holds test-device shafts in position as partial reservoir-cap-hole closures.

32 Claims, 7 Drawing Sheets

MULTI-SITE SKIN-TEST SYSTEM AND METHOD

FIELD OF THE INVENTION

This invention relates generally to: an improved system for making multi-site skin tests; new and improved components used in the system; and a method of using the system.

BACKGROUND OF THE INVENTION

U.S. Pat. Nos. 5,738,108 and 5,792,071, which issued to Applicant and which are incorporated herein by reference, are directed to various components of a system including a multi-site skin-test device, a tray of reservoirs for holding allergenic extract, and a tray lid.

Figure 1:
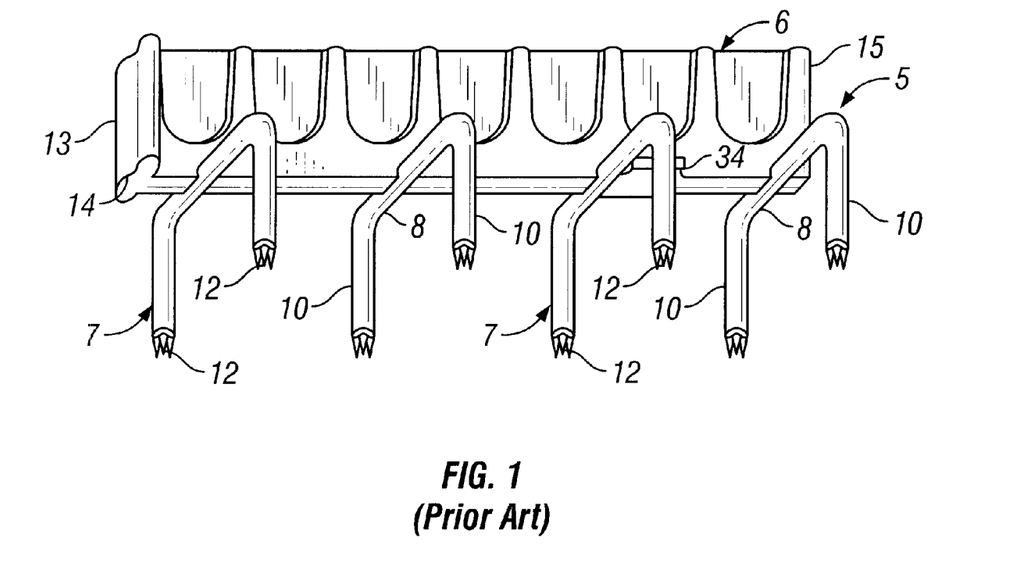
FIG. 1 shows a prior art multi-site skin-test device.

A test device, also referred to herein as an applicator, of such a system is depicted in FIG. 1. The test device 5, includes an elongated handle 6. Multiple inverted U-shaped limbs 7 extend outwardly and downwardly from the handle 6. Each limb 7 includes a horizontal bight section 8 attached approximately at its mid-point to the underside of the handle 6 and a pair of downwardly extending legs 10. The distal ends of legs 10 lie in approximately the same plane, and each end has skin puncturing points indicated generally at 12. For example, the points 12 may take the form of nine pressure-type sharp points clustered closely together to create a capillary effect between the points for holding liquid in the interstices or spaces between the points as disclosed in Kravitz U.S. Pat. No. 3,136,314. The disclosure of U.S. Pat. No. 3,136,314 is incorporated herein by reference. The cross-sectional size of the legs 10 does not appreciably exceed the cross-sectional size of the points 12.

The handle 6 includes a guide formation 13 that extends generally transversely to the handle 6. The guide formation 13 includes a vertically extending concave groove or recess 14. Preferably, the applicator 5 will be integrally molded, such as by injection molding, from a suitable plastic. It could be formed, however, from other materials by other methods. By injection molding the applicator 5 from a plastic, the cost of these units can be reduced to a point at which the applicators are disposable after a single use. The applicators 5, therefore, can be sterilized before shipment. A healthcare worker can then open the packages, use the sterilized applicators, and discard the applicators immediately after using them.

Figure 2:
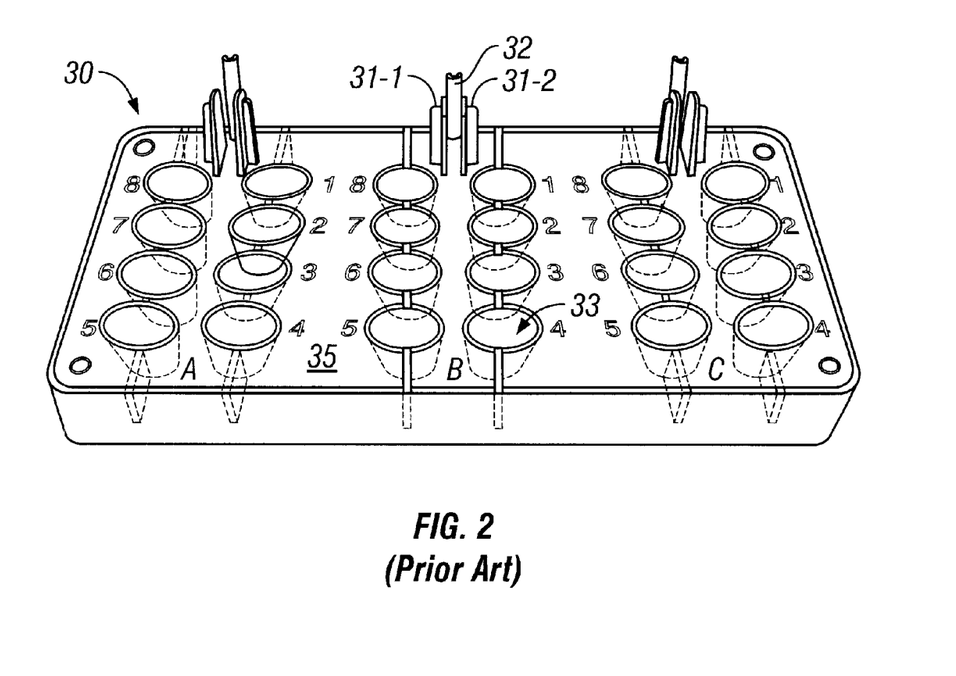
FIG. 2 shows a prior art reservoir tray designed for use without reservoir caps.

The system also includes a tray 30, depicted in FIG. 2, for use in accordance with such an applicator or test device 5. The tray 30 has an upper surface 35. Twenty-four reservoirs 33, which extend downwardly from surface 35, are arranged in a repeating pattern that corresponds to the patterns of the distal points 12 of the test device 5. The reservoirs are used for storing allergenic skin test solutions to be loaded onto the pointed ends 12 of the test device 5. The reservoirs 33 are grouped into three batteries, labeled A, B, and C, each including eight reservoirs.

Figure 3:
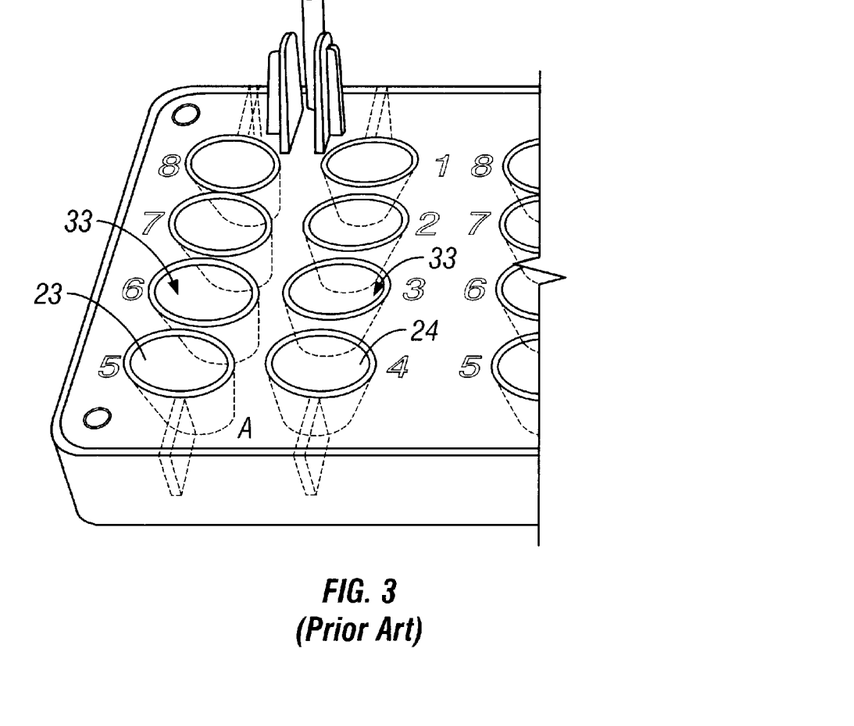
FIG. 3 is an enlarged view of one battery of prior art reservoirs designed for use without reservoir caps.

Referring to FIG. 3, the eight reservoirs of a particular battery are labeled one through eight starting with the reservoir in the upper-right-hand corner and proceeding clockwise. As discussed in more detail in Applicant's U.S. Pat. No. 5,792,071, the reservoirs 33 each have a semi-cylindrical upwardly extending interior half 23 and an opposite inclined side 24 that is generally semi-conical.

Referring again to FIG. 2, to help a system user quickly and accurately guide the pointed ends 12 properly into each of the reservoirs 33, each of the three batteries or sets of reservoirs 22 in the tray 30 is provided with an upright orienting pin 32. The orienting or guide formation 13 on the handle 6 of the test device 5 is co-operable with the guide or orienting pin 32. When the handle 6 of the test device 5 is inserted between the pair of upright parallel tabs 31 and the guide formation 13 of the handle is placed against the guide pin 32, the test device can then be lowered properly aligned with the battery of reservoirs. When the test device 5 is lowered in proper alignment, each vertical leg 10 will be oriented so that its pointed ends 12 will be directly over the bottom of a reservoir 33. Each pair of tabs 31 is located such that when the guide formation 13 on of the test device 5 engages an orienting pin 32 the vertical edges of the tabs 31 nearer to the pin 32 will be engaged by the horizontal portions of the limbs 7 nearest the pin 32. Thus, each pin 32, each guide formation 13, each pair of limbs 7 juxtaposed to the formation 13, and each pair of tabs 31 jointly cooperate to readily guide and orient each test device 5 with respect to a set of reservoirs 33.

Applicant's U.S. Pat. No. 5,738,108 discloses including formations 34 on opposite sides along the bottom edge of the test device's handle 6 to prevent the test device 5 from being inserted into the tray rotated 180 degrees from its proper orientation, which would undesirably result in the points 12 picking up test solutions from the wrong reservoirs 33. The formations 34 protrude from opposite sides of the handle 6 and are positioned such that they will engage the upper ends of the guide tabs 31 if a user attempts to insert the test device 5 wrong-end-to.

Figure 4:
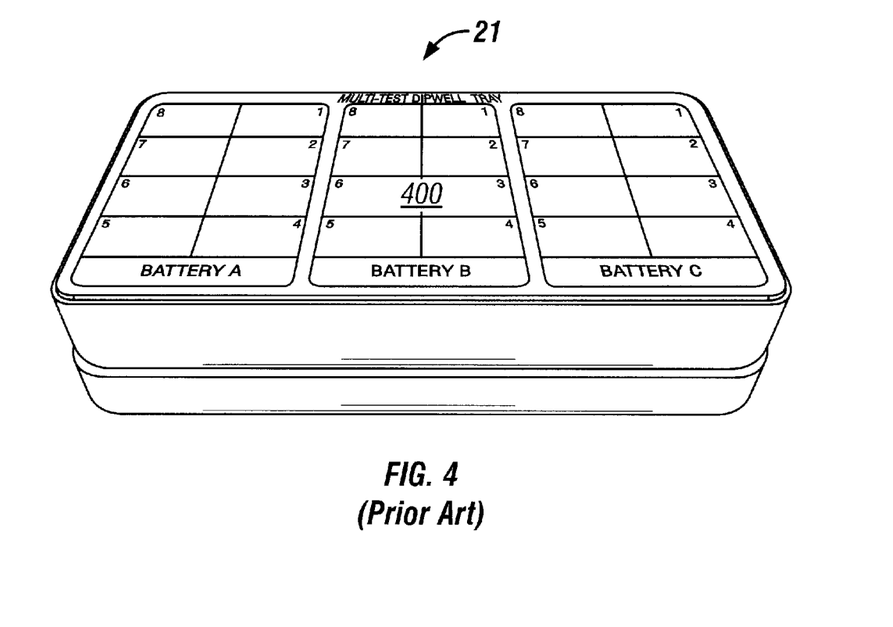
FIG. 4 is a perspective view of a prior art adhesive-backed label on top of a prior art reservoir-tray lid.

Referring to FIG. 4, the system may further comprise an adhesive-backed label 400 placed onto a lid or cover 21 that preferably forms an airtight seal when placed over the tray 30. Trays covered with lids 21 can be stacked to save space in refrigerators used to store the trays when they have been filled with skin test solutions and are not in use.

A shortcoming of the system described above is that test solution can be spilled from the reservoirs when the tray is bumped, otherwise moved abruptly, tilted onto its side, and the like.

Figures 5, 6:
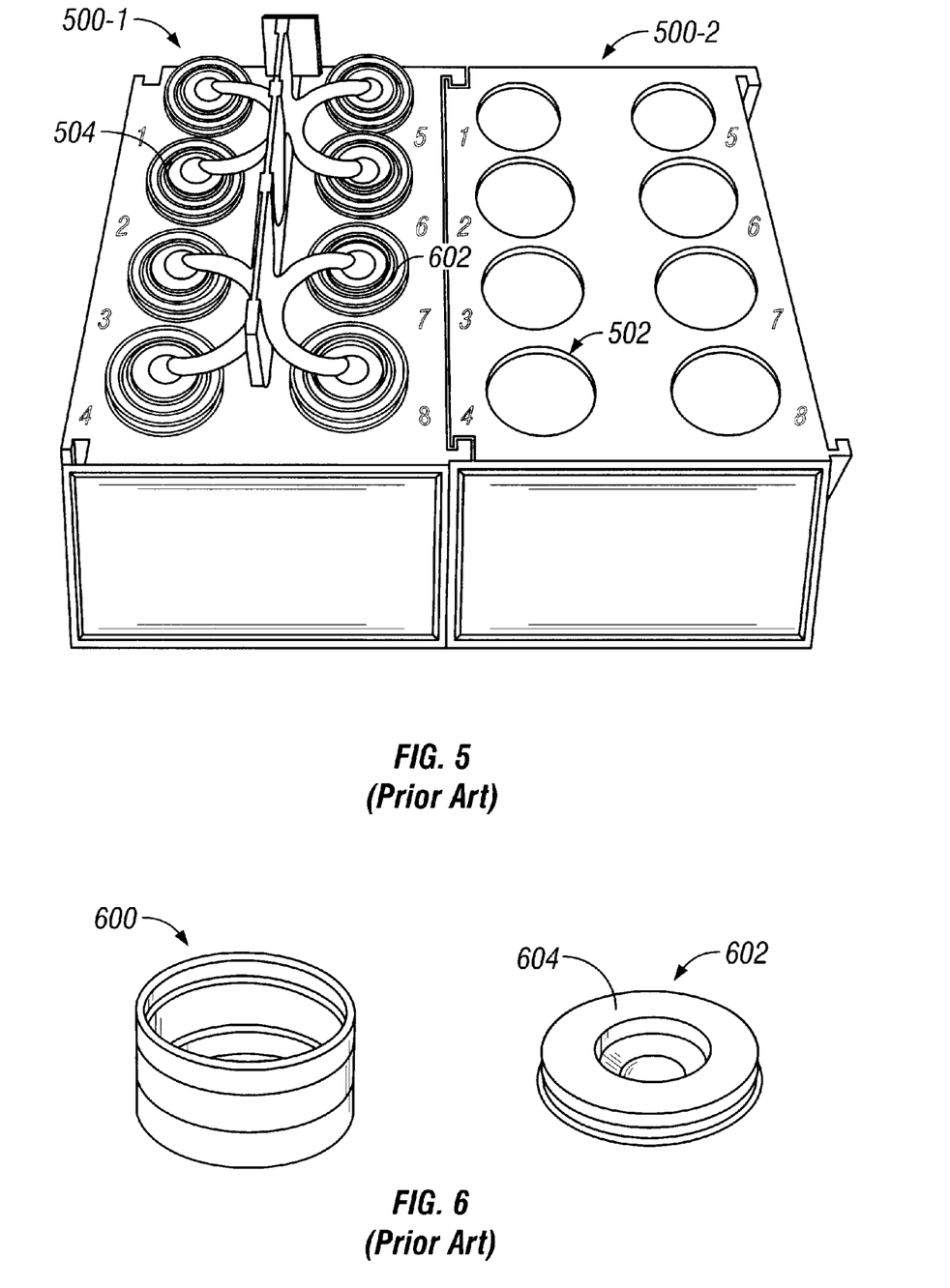
FIG. 5 is a perspective view of a prior art capped-reservoir system.
FIG. 6 is an enlarged perspective view of the prior art two-piece well and cap of the system shown in FIG. 5.

Other conventional systems include capped reservoirs. For instance, FIG. 5 depicts a system available from Panatrex, Inc. of Placentia, Calif. Referring to FIG. 6, the Panatrex system includes multiple wells 600 and well lids 602. The manufacturer typically places well lids 602 onto wells 600 individually. This is an undesirably time-consuming process, which, of course, produces a corresponding undesirable manufacturing-cost component. Referring again to FIG. 5, the consumer, a healthcare professional, must insert each of the assembled well-and-lid combinations individually into a corresponding hole 502 in the reservoir-holding tray 500. Closure caps 504, which are located on the test device limbs, rest on a circular ridge 604 (FIG. 6) of each lid 602. In use, however, test solutions tend to undesirably accumulate around the well openings and ultimately adhere to the test device's closure caps 504 in systems of the type shown in FIG. 5.

Cost and ease and speed of use are important factors considered by healthcare professionals when they are deciding which allergy skin test system to use. A need, therefore, exists in the prior art for a cost-effective pre-assembled skin-test system having capped reservoirs that overcomes the foregoing shortcomings of prior art multi-site skin-test systems.

BRIEF SUMMARY OF THE INVENTION

In accordance with an illustrative embodiment of the invention, a multi-site allergy-skin-testing system includes a tray with reservoirs having an upwardly facing ledge surface. The ledge extends outwardly from an inner surface of an upper portion of the reservoirs. A bottom downwardly facing surface of each reservoir cap is adapted to rest on the upwardly facing ledge surface of the reservoirs. The upper portion of each reservoir is preferably adapted to receive a reservoir cap so that a relatively tight fit is achieved between the inserted reservoir caps and the upper portion of the reservoirs. The tight fit between the upper portion of the reservoirs and the reservoir caps advantageously eliminates the need for time-consuming and expensive manufacturing processes, such as ultrasonically welding the caps to the reservoirs.

The system also comprises a strip of interconnected reservoir caps. The caps of a strip are interconnected with one another via connection members. Each reservoir cap includes an upper surface and a tapered surface extending from the upper surface toward a lower surface, thereby defining a generally conically shaped depression having a circular hole at the bottom. The generally conically shaped depression and circular hole are collectively referred to herein as a tapered bore. The tapered bore preferably extends downwardly approximately the same distance as the height of a side surface of a reservoir cap.

The outer side surfaces of the caps are preferably adapted to fight tightly within the inside surfaces of corresponding upper portions of the reservoirs. The outer side surface of each cap preferably includes a slight draft or taper. Each of the upper portions of the reservoirs also preferably has a slight draft or taper corresponding to the slight draft or taper of the outer surface of each of the caps. The lower portion of the outside surface of each side of the caps preferably includes a beveled surface. A strip of caps having such beveled surfaces may advantageously be set in place by hand such that substantially only the beveled surfaces are inserted into the upper portions of the reservoirs. A machine, such as a pneumatic machine, may then be used to press the strip of caps into the reservoirs substantially simultaneously so that the top surfaces of the caps are substantially flush with the top surface of the tray. This process is significantly less time-consuming and significantly more cost-effective than inserting reservoir caps individually, and it results in healthcare professionals receiving a fully assembled product.

The tapered surfaces of the reservoir caps advantageously prevent skin-test solutions from splashing out of the reservoirs when the tray is moved abruptly. When inserted into the reservoirs, test device shafts partially close the reservoir cap holes, thereby preventing skin-test solutions from coming out of the reservoirs. When the tray, with strips of reservoir caps inserted into the tray, is tilted, even onto its side, test solutions will not come out of their wells because of the capillary attraction between the shaft and the circumference of the reservoir-cap holes. In this manner, test solutions accumulating around well openings and ultimately adhering to the test devices is advantageously avoided.

A guidance system cooperates with the tapered surface of the reservoir caps to provide additional clearance space for the pointed ends of the test device as the pointed ends are lowered into the reservoirs.

The system may further include a lid for the tray. The inside surface of the top of the lid may have a downwardly extending ridge. The downwardly extending ridge, cooperates with upright parallel tabs of the guidance system to prevent a user from putting the lid on top of tray rotated 180 degrees from its proper orientation, or, in other words, with the lid's front and back sides reversed. The ridge also holds the test devices in place on the tray so that the shafts stay in position to serve as partial closures for the reservoir-cap holes.

A method, in accordance with an illustrative embodiment of the invention, of using a multi-site skin-testing system may include: removing a tray having pre-installed reservoir caps, each cap having a hole, from the tray's packaging; at least partially filling the capped reservoirs with allergenic extract; inserting the shafts of a skin test device into the capped reservoirs so that the test device's shafts partially close the reservoir cap holes; and performing a multi-site skin test using the test device without having to insert caps onto or into the reservoirs. The shafts of a second sterile skin test device may then be inserted into the capped reservoirs so that the second test device's shafts partially close the reservoir cap holes. A lid, having a downwardly extending ridge, may then be placed onto the tray to hold the test device shafts in place in the reservoir-cap holes during transporting and storage.

DETAILED DESCRIPTION OF AN ILLUSTRATIVE EMBODIMENT OF THE INVENTION

Figure 7:
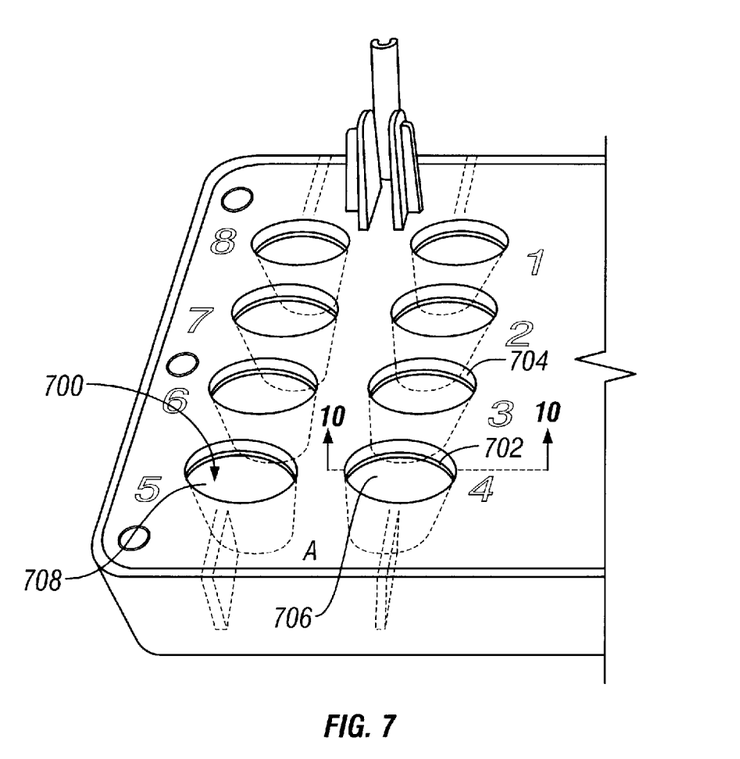
FIG. 7 is an enlarged view of reservoirs of a multi-site skin-testing system in accordance with an illustrative embodiment of the invention.

FIG. 7 depicts a battery, labeled A, of eight reservoirs 700 in accordance with an illustrative embodiment of the invention. The reservoirs include an upwardly facing ledge surface 702 that substantially surrounds the circumference of an upper portion of the reservoirs. The ledge 702 extends outwardly from an inner surface 704 of an upper portion of the reservoirs 700. The distance that the ledge 702 extends from the inner surface 704 gradually varies from a relatively smaller distance on the semi-cylindrical side 706 of each reservoir 700 to a relatively larger distance on the semi-conical side 708 of each reservoir 700. The upper portion of each reservoir 700 is preferably adapted to receive a reservoir cap 802 (FIG. 8) so that a relatively tight fit is achieved between the inserted reservoir cap 802 and the upper portion of the reservoirs 700. The tight fit may be accomplished by making the outer dimensions of a reservoir cap 802 substantially the same as the inner dimensions of an upper portion of the reservoir 700. As will be apparent, other suitable tolerances could also be used. For instance, the outer dimensions of a side surface 812 of a reservoir cap 802 could be no more than 0.0005" less than the inner dimensions of the inner surface 704 of an upper portion of the reservoir 700. The tight fit between the upper portion of the reservoirs 700 and the reservoir caps 802 advantageously eliminates the need for time-consuming and expensive manufacturing processes, such as ultrasonically welding the caps to the reservoirs.

Figure 8:
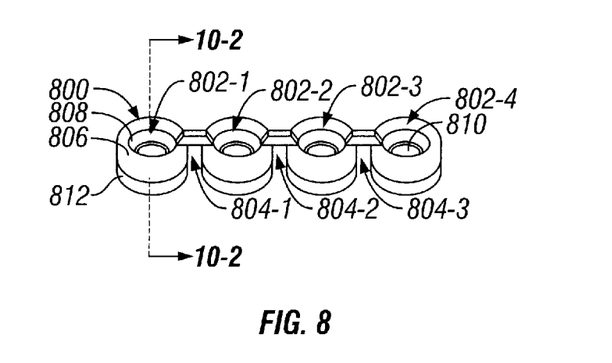
FIG. 8 is a perspective view of a strip of reservoir caps of a multi-site skin-testing system in accordance with an illustrative embodiment of the invention.

FIG. 8 depicts a strip of interconnected reservoir caps 800 in accordance with an illustrative embodiment of the invention. Each reservoir cap 802-1 through 802-4 is interconnected with one or two other reservoir caps 802 of the strip 800 via connection members 804-1 through 804-3. Each reservoir cap 802 includes an upper surface 806 and a tapered surface 808 extending from the upper surface 806 toward a lower surface 900 (FIG. 9), thereby defining a generally conically shaped depression having a circular hole 810 at the bottom. The generally conically shaped depression and circular hole 810 are collectively referred to herein as a tapered bore. The tapered bore preferably extends downwardly approximately the same distance as the height of side surface 812 of reservoir cap 802. The outer side surface 812 is preferably adapted to fight tightly within the inside surface 704 of an upper portion of reservoir 700, as discussed above.

Figure 10:
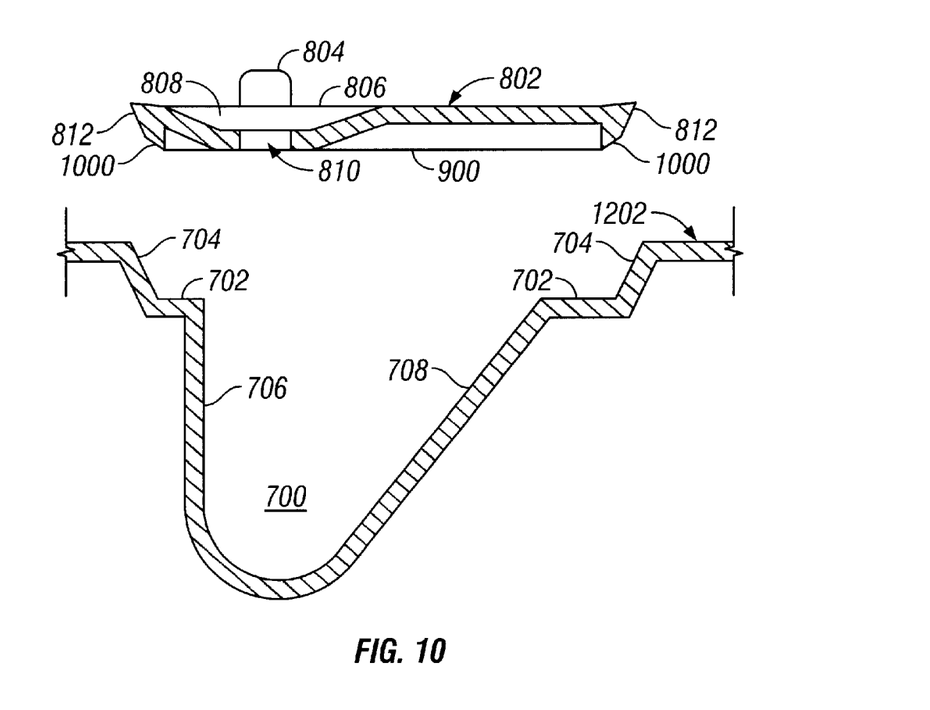
FIG. 10 is a cross-sectional view of a strip of caps above a reservoir taken along view lines 10-1 and 10-2 of FIGS. 7 and 8.

FIG. 10 is a cross-sectional view of a strip of caps above a reservoir taken along view lines 10-1 and 10-2 of FIGS. 7 and 8. The cap 802 includes a tapered surface 808 and a circular hole 810 that together define a tapered bore, as discussed above.

The outer side surface 812 of the cap 802 includes a slight draft or taper, which is shown greatly exaggerated in FIG. 10 for illustrative purposes. The slight draft or taper may be at an angle of approximately 1 degree. As will be apparent, other suitable angles could also be used. The inner side surface 704 of the upper portion of reservoir 700 preferably also has a corresponding slight draft or taper at substantially the same angle as the slight draft or taper of the outer side surface 812 of the cap 802.

A lower portion of the outside surface 812 of the side of the cap 802 may include a beveled surface 1000. Beveled surface 1000 may be formed at an angle of approximately 20 degrees relative to the outer side surface 812. As will be apparent, bevel 1000 is depicted in FIG. 10 having an angle much greater than 20 degrees for illustrative purposes. Of course, other suitable angles could also be used.

Figure 11:
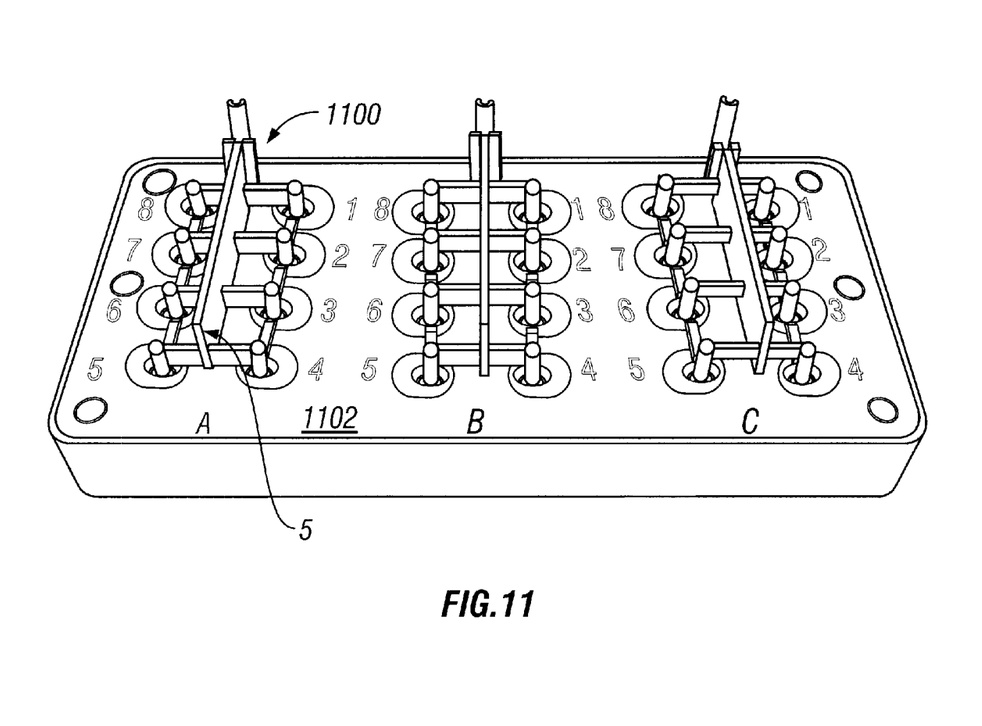
FIG. 11 is a perspective view of a reservoir tray with strips of reservoir caps inserted into the reservoirs and showing test devices inserted into the reservoirs of a multi-site skin-testing system in accordance with an illustrative embodiment of the invention.

A strip of caps 800 having such beveled surfaces 1000 may advantageously be set in place by hand such that substantially only the beveled surfaces 1000 are inserted into the upper portions of the reservoirs 700. A machine, such as a pneumatic machine, may then be used to press the strip of caps 800 into the reservoirs substantially simultaneously so that the top surfaces 806 of the caps 802 are substantially flush with a top surface 1102 (FIG. 11) of a tray 1100. This process is significantly less time-consuming than inserting reservoir caps individually and results in healthcare professionals receiving a cost-effectively produced fully assembled product.

Figure 9:
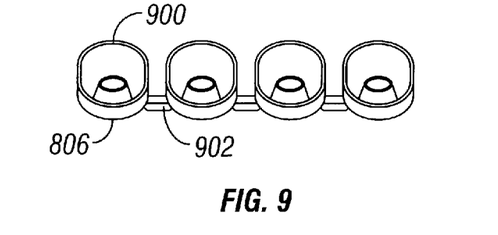
FIG. 9 is a perspective view of the strip of reservoir caps shown in FIG. 8 turned upside-down.

FIG. 9 is a perspective view of the strip of interconnected reservoir caps 800 of FIG. 8 turned upside-down. A bottom downwardly facing surface 900 of each reservoir cap 802 is adapted to rest on the upwardly facing ledge surface 702 of the reservoirs 700. Similarly, referring to FIGS. 8-11, when a strip of interconnected reservoir caps 800 is inserted into a row of reservoirs 700, a bottom surface 902 of connection member 804 is supported by an upper surface 1102 of reservoir tray 1100. Reservoir tray 1100 is similar to reservoir tray 30 of FIG. 2. Reservoirs 33 of tray 30, however, are replaced in reservoir tray 1100 with reservoirs 700 that have reservoir cap strips 800 inserted. Three test devices 5 are also depicted with their pointed ends 12 inserted through the reservoir-cap holes 810 and into the reservoirs 700.

Figure 12:
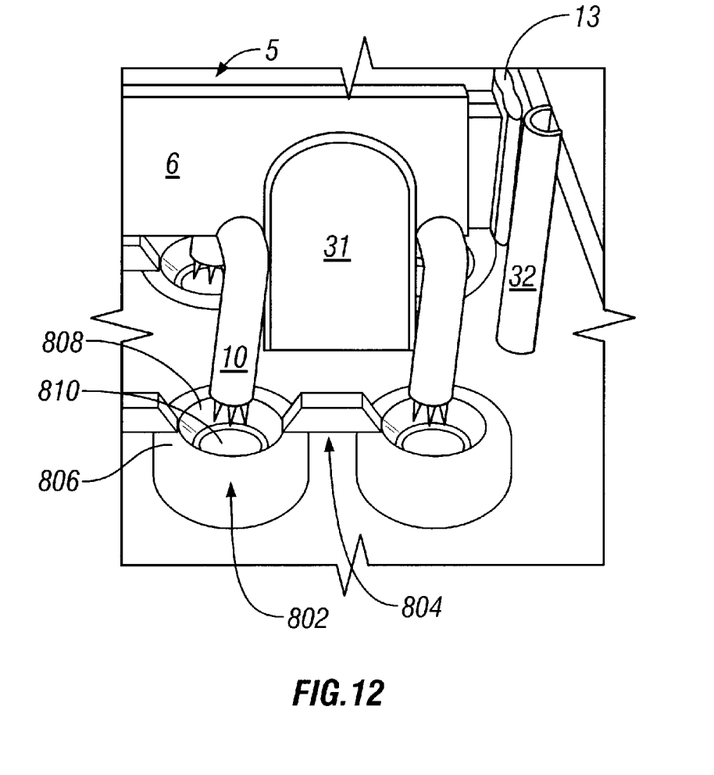
FIG. 12 shows cooperation of a guidance system and the tapered bores of a strip of reservoir caps to prevent damage to the pointed ends of a test device of a multi-site skin-testing system in accordance with an illustrative embodiment of the invention.

Referring to FIG. 12, the guidance system, which includes the guide formation 13, the upright parallel tabs 31, and the orienting pin 32, cooperates with the tapered surface 808 of the reservoir caps 802 to provide additional clearance space for the pointed ends 12 of the test device 5 as the pointed ends 12 are lowered into the reservoirs 700. This additional clearance space would not be present absent the generally conically shaped depression formed by tapered surface 808. In FIG. 12, the bottom portion of shaft 10 of the test device 5 is shown lowered into the conically shaped depression created by the tapered surface 808. As the device 5 is lowered further into the guidance system, the tolerances preferably become tighter and, consequently, point damage does not occur.

The tapered surface 808 of the reservoir caps 802 advantageously prevents skin-test solutions from splashing out of the reservoirs 700 when the tray 1100 is moved abruptly. When inserted into the reservoirs 700, test device shafts 10 partially close the reservoir cap holes 810, thereby preventing skin-test solutions from coming out of the reservoirs 700. When the tray 1100, with strips of reservoir caps 800 inserted into the tray, is tilted, even onto its side, test solutions will not come out of their wells because of the capillary attraction between the shaft 10 and the circumference of the reservoir cap holes 810. In this manner, test solutions accumulating around well openings and ultimately adhering to the test devices is advantageously avoided. The testing solutions are typically 50% glycerin, which provides a viscosity suitable for the type of capillary attraction described above.

Figure 13:
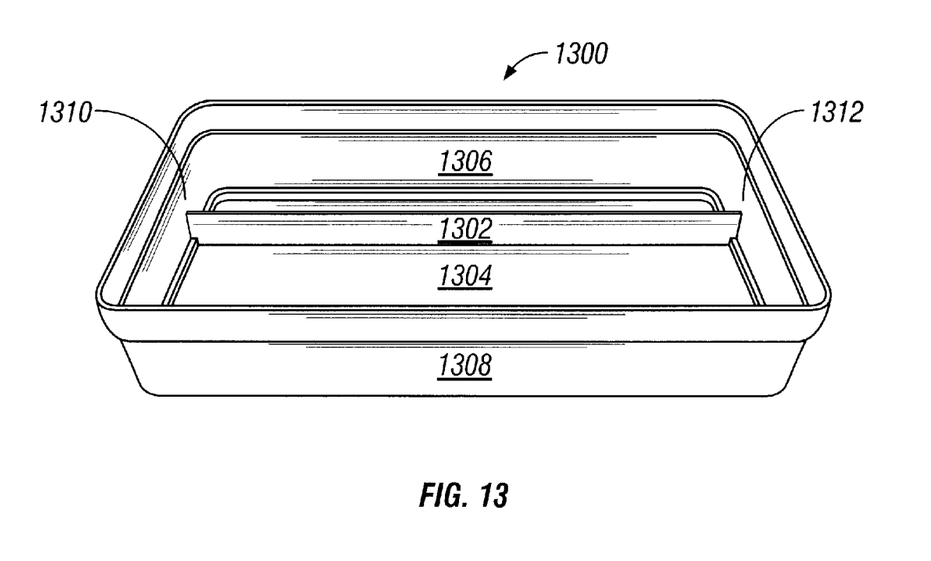
FIG. 13 is a perspective view of an upside-down tray lid of a multi-site skin-testing system in accordance with an illustrative embodiment of the invention.

FIG. 13 is a perspective view of an upside-down lid 1300 in accordance with an illustrative embodiment of the invention. Ridge 1302 extends downwardly from the top 1304 of lid 1300, which also includes front 1306, back 1308, left 1310, and right 1312 sides. The downwardly extending ridge 1302, cooperates with upright parallel tabs 31 to prevent a user from putting the lid 1300 on top of tray 1100 rotated 180 degrees from its proper orientation. Absent ridge 1302, if the lid were placed on the tray rotated 180 degrees from its proper orientation, the adhesive-backed label 400 would incorrectly identify which solutions were in which wells in the tray underneath. Stated differently, ridge 1302 cooperates with upright parallel tabs 31 to ensure that lid 1300 is not placed onto tray 1100 backwards, that is, with the left and right sides reversed. Ridge 1302 also holds the test devices 5 in place on the tray 100 so that the shafts 10 stay in position to serve as partial closures for the reservoir-cap holes 810.

Figure 14:
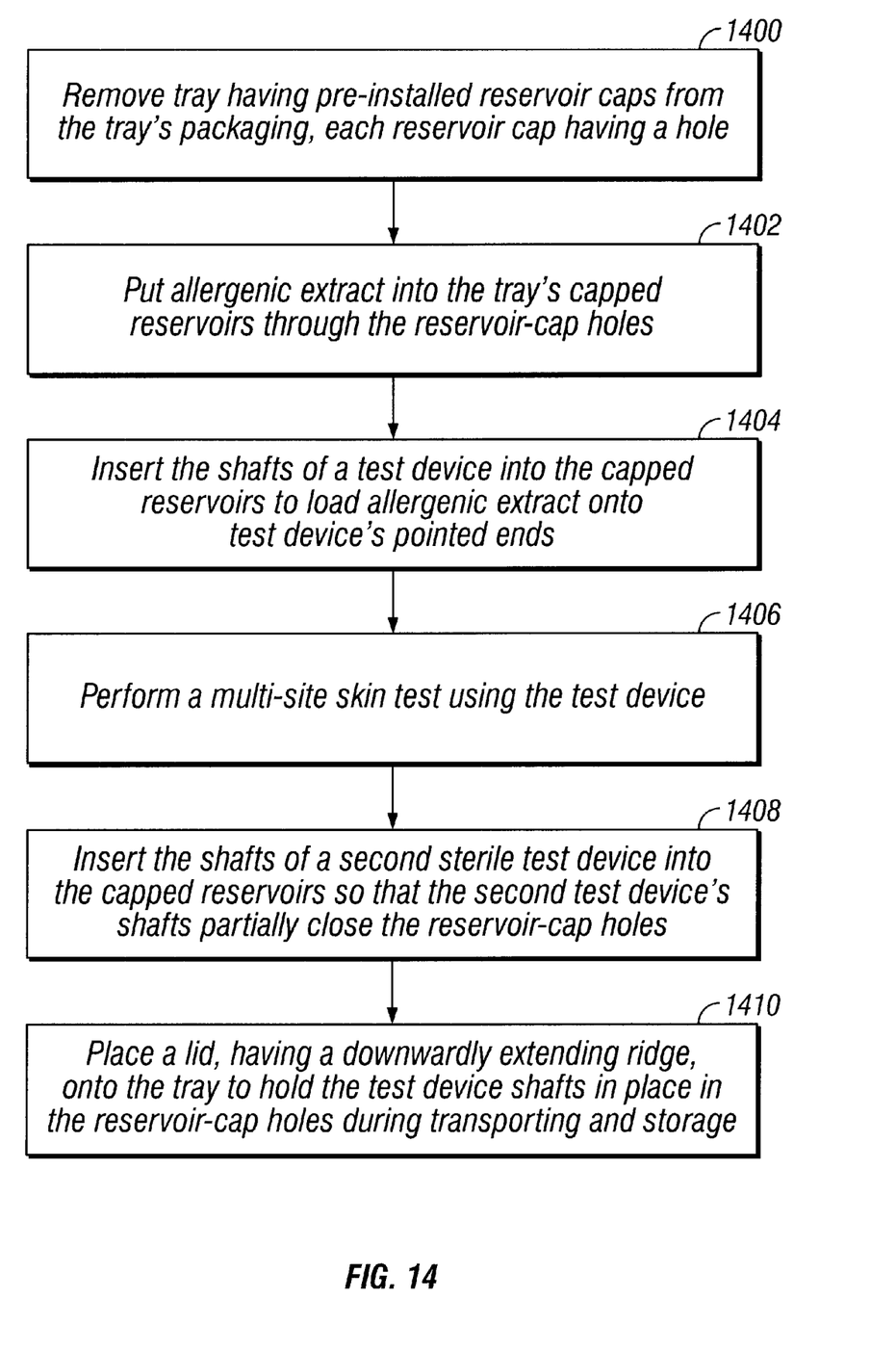
FIG. 14 is a flowchart showing steps of using a multi-site skin-testing system in accordance with an illustrative embodiment of the invention.

FIG. 14 is a flowchart showing steps of using a multi-site skin-testing system in accordance with an illustrative embodiment of the invention. As depicted at 1400, a healthcare worker removes a tray having pre-installed reservoir caps, each cap having a hole, from the tray's packaging. As depicted at 1402, the capped reservoirs are at least partially filled with allergenic extract. As depicted at 1404, the shafts of a skin test device are then inserted into the capped reservoirs to load allergenic extract onto the test device's pointed ends. A multi-site skin test is then performed using the test device, as depicted at 1406. Advantageously, reservoirs and caps do not have to be inserted into the tray. As depicted at 1408, the shafts of a second sterile skin test device are then inserted into the capped reservoirs so that the second test device's shafts partially close the reservoir cap holes. As depicted at 1410, a lid, having a downwardly extending ridge, is placed onto the tray to hold the test device shafts in place in the reservoir-cap holes during transporting and storage. The tray, lid, and one or more test devices can then be stored with the lid's downwardly extending ridge holding the test-device shafts in place as partial reservoir-cap-hole closures, as described above.

While the invention has been described with respect to specific examples including presently preferred modes of carrying out the invention, those skilled in the art will appreciate that there are numerous variations and permutations of the systems and techniques described above that fall within the spirit and scope of the invention as set forth in the appended claims.

I claim:

1. A system for storing and applying allergenic extracts, the system comprising:
    at least one multi-site skin-test device having pointed ends;
    a reservoir tray having a plurality of reservoirs for holding allergenic extracts in the reservoirs to be withdrawn therefrom by the pointed ends of the test device in relatively small increments; and
    at least one strip of interconnected reservoir caps inserted into the plurality of reservoirs, wherein the reservoir caps include cap holes through which a plurality of shafts of the test device are inserted to withdraw the allergenic extracts from the reservoirs.

2. The system of claim 1 wherein the reservoir tray and the plurality of reservoirs are integrally formed.

3. The system of claim 2 wherein the reservoir tray and the reservoirs are injection-molded.

4. The system of claim 1 wherein the at least one strip of interconnected reservoir caps comprises four interconnected reservoir caps.

5. The system of claim 1 wherein at least one reservoir cap includes a tapered bore having a relatively larger diameter at an upper surface of the reservoir cap and a relatively smaller diameter at a lower surface of the reservoir cap.

6. The system of claim 5, wherein the reservoir tray further comprises a guidance system that prevents improperly oriented test devices from being inserted into the reservoirs, wherein the at least one tapered bore cooperates with the guidance system to prevent damage to the test device's pointed ends.

7. The system of claim 5, wherein the at least one tapered bore is defined by a reservoir-cap surface that acts as a barrier to prevent at least one of the allergenic extracts from splashing out of at least one of the reservoirs when the reservoir tray is moved abruptly.

8. The system of claim 5, wherein at least one shaft of the test device cooperates with the at least one tapered bore to prevent at least one of the allergenic extracts from spilling out of the reservoir trays.

9. The system of claim 8, wherein an outer diameter of at least one test-device shaft is less than the diameter of the lower surface of at least one of the tapered bores such that capillary attraction between the test-device shaft and the diameter of the lower surface of the tapered bore prevents at least one skin-test substance from spilling out of at least one of the reservoirs even when the tray is tipped 90 degrees from a horizontal orientation.

10. The system of claim 1 wherein the reservoir caps have outer dimensions substantially the same as inner dimensions of an upper portion of the reservoirs such that the at least one strip of reservoir caps is held in place in the reservoirs by friction between respective outer side surfaces of the reservoir caps and corresponding inner surfaces of the reservoirs.

11. The system of claim 1 wherein at least one reservoir includes an upwardly facing ledge surface that supports a downwardly facing bottom surface of at least one of the reservoir caps.

12. The system of claim 1 wherein an outer side surface of at least one of the reservoir caps has a slight draft or taper.

13. The system of claim 1 wherein an upper portion of at least one of the reservoirs includes an inner surface having a slight draft or taper corresponding to the slight draft or taper of at least one of the reservoir caps.

14. The system of claim 1 wherein a lower portion of an outer side surface of at least one of the reservoir caps has a beveled surface.

15. The system of claim 1, wherein the reservoir tray further comprises a guidance system that prevents improperly oriented test devices from being inserted into the reservoirs.

16. The system of claim 15, further comprising a tray lid having a ridge that extends downwardly to hold at least one test device in place in the reservoirs when the lid is placed onto the reservoir tray.

17. The system of claim 16, wherein the guidance system includes at least one formation projecting upwardly from an upper surface of the reservoir tray such that the reservoir tray's upwardly projecting formation cooperates with the tray lid's downwardly extending ridge to prevent the lid from being placed onto the reservoir tray in an improper orientation.

18. A reservoir tray for storing allergy-skin-test solutions in multiple reservoirs to be loaded onto pointed ends of at least one multi-site skin-test device, the reservoir tray comprising:
    an upper surface; and
    a plurality of reservoirs extending downwardly from the upper surface for holding relatively large volumes of allergenic extracts in the reservoirs to be withdrawn therefrom by the pointed ends of the test device in relatively small increments, wherein at least one reservoir includes an upwardly facing ledge surface for supporting a bottom surface of at least one strip of interconnected reservoir caps that are insertable into the plurality of reservoirs, wherein the reservoir caps include cap holes through which a plurality of shafts of the test device are inserted to withdraw the allergenic extracts from the reservoirs.

19. The reservoir tray of claim 18 wherein the reservoir tray and the plurality of reservoirs are integrally formed.

20. The reservoir tray of claim 19 wherein the reservoir tray and the reservoirs are injection-molded.

21. The system of claim 19 wherein an outer side surface of at least one of the reservoir caps has a slight draft or taper.

22. The system of claim 19 wherein a lower portion of an outer side surface of at least one of the reservoir caps has a beveled surface.

23. The reservoir tray of claim 18, wherein the reservoir tray further comprises a guidance system that prevents improperly oriented test devices from being inserted into the reservoirs, wherein the at least one tapered bore cooperates with the guidance system to prevent damage to the test device's pointed ends.

24. A strip of interconnected reservoir caps adapted for substantially simultaneous insertion into a plurality of reservoirs for holding a plurality of allergenic extracts, the strip of reservoir caps comprising:

a plurality of reservoir caps each having a hole; and a plurality of connection members connecting the reservoir caps to one another.

25. The strip of interconnected reservoir caps of claim 24 wherein the strip of interconnected reservoir caps comprises four interconnected reservoir caps connected by three connection members.

26. The strip of interconnected reservoir caps of claim 24 wherein at least one of the reservoir-cap holes comprises a tapered bore having a relatively larger diameter at an upper surface of the reservoir cap and a relatively smaller diameter at a lower surface of the reservoir cap.

27. A reservoir-tray lid for use with a reservoir tray for storing allergy-skin-test solutions in multiple reservoirs to be loaded onto pointed ends of at least one multi-site skin-test device, the reservoir-tray lid comprising:

a top;

four sides; and at least one ridge extending downwardly from the top of the lid to hold at least one test device in place in the reservoirs when the lid is placed onto the reservoir tray.

28. The reservoir-tray lid of claim 27, wherein the reservoir tray includes a guidance system having at least one formation projecting upwardly from an upper surface of the reservoir tray such that the reservoir tray's upwardly projecting formation cooperates with the tray lid's downwardly extending ridge to prevent the lid from being placed onto the reservoir tray in an improper orientation.

29. A method of using a multi-site skin-test system having a tray of capped reservoirs for holding allergenic extract to be loaded onto a test device, the method comprising:

removing the tray from a package, wherein the tray has a plurality of pre-installed caps inserted into the reservoirs and the caps each include a cap hole;

putting allergenic extract into at least one of the reservoirs through at least one of the reservoir-cap holes;

inserting a plurality of shafts of the skin test device through a corresponding plurality of the reservoir-cap holes; and performing a multi-site skin test using the test device without inserting any caps onto or into the reservoirs.

30. The method of claim 29 further comprising:

inserting a plurality of shafts of a second skin test device through a corresponding plurality of reservoir-cap holes so that the second test device's shafts partially close the reservoir-cap holes; and placing a lid over the tray, the lid having a downwardly extending ridge that cooperates with a handle of the test device to keep the test-device shafts positioned within the reservoir-cap holes.

31. The method of claim 30 wherein the step of inserting the plurality of shafts of the second skin test device through the corresponding plurality of reservoir-cap holes further comprises using a guidance system that projects upwardly from the tray and prevents the second test device from being inserted into the reservoirs oriented improperly.

32. The method of claim 31 wherein the lid's downwardly extending ridge and the tray's upwardly projecting guidance system cooperate to prevent the lid from being placed onto the tray aligned improperly.

* * * * *